United States Patent [19]
Presant et al.

[11] Patent Number: 5,019,369
[45] Date of Patent: May 28, 1991

[54] METHOD OF TARGETING TUMORS IN HUMANS

[75] Inventors: Cary A. Presant, San Marino; Richard T. Proffitt, Arcadia, both of Calif.

[73] Assignee: Vestar, Inc., San Dimas, Calif.

[21] Appl. No.: 279,316

[22] Filed: Dec. 1, 1988

Related U.S. Application Data

[63] Continuation of Ser. No. 674,201, Nov. 23, 1984, abandoned, and a continuation-in-part of Ser. No. 663,503, Oct. 22, 1984, abandoned, and a continuation-in-part of Ser. No. 663,550, Oct. 22, 1984, abandoned, and a continuation-in-part of Ser. No. 363,593, Mar. 30, 1982, abandoned.

[51] Int. Cl.$^5$ .................. A61K 43/00; A61K 9/133; A61K 49/02
[52] U.S. Cl. .......................... 424/1.1; 424/9; 424/450; 428/402.2; 436/829; 600/3
[58] Field of Search .................. 424/1.1, 9, 450

[56] References Cited

U.S. PATENT DOCUMENTS

| | | | |
|---|---|---|---|
| 3,992,513 | 11/1976 | Petkau et al. | 424/1.1 |
| 4,086,330 | 4/1978 | Petkau et al. | 424/1.1 |
| 4,310,505 | 1/1982 | Baldeschwieler et al. | 424/1.1 |
| 4,310,506 | 1/1982 | Baldeschwieler et al. | 424/1.1 |
| 4,429,008 | 1/1984 | Martin et al. | 424/1.1 |
| 4,485,054 | 11/1984 | Mezei et al. | 424/1.1 |
| 4,497,791 | 2/1985 | Gamble et al. | 424/1.1 |
| 4,544,545 | 10/1985 | Ryan et al. | 424/9 |
| 4,581,222 | 4/1986 | Baldeschwieler et al. | 424/1.1 |
| 4,588,578 | 5/1986 | Fountain et al. | 424/1.1 |

OTHER PUBLICATIONS

Proffitt et al., Journal of Nuclear Medicine, 24(1), pp. 45-51 (Jan. 1983).
Richardson et al., Journal of Nuclear Medicine, 19(9), pp. 1049-1054 (1978).
Wu et al., Proc. Natl. Acad. Sci. U.S.A., 78, pp. 2033-2037, (1981).
Mauk et al., Proc. Natl. Acad. Sci. U.S.A., 76, pp. 765-769, (1979).
H. I. Peterson, Vascular and Extravascular Spaces in Tumors: Tumor Vascular Permeability.
G. Gregoriadis, Liposomes in Biological Systems, Gregoriadis, Ed. Ch. 2 (1980).
B. Ryman et al., Biol. Cell, vol. 47, pp. 71-80 (1983).
G. Poste, Biol. Cell, vol. 47, pp. 19-38 (1983).
Mauk & Gamble, Anal. Biochem., 94, pp. 302-307 (1979).

*Primary Examiner*—Robert L. Stoll
*Assistant Examiner*—John M. Covert
*Attorney, Agent, or Firm*—Lyon & Lyon

[57] ABSTRACT

A method is provided for delivering micellular particles containing a radiolabelled marker to tumors within humans. The micellular particles are less than approximately 2000Å and incorporate essentially chemically pure phospholipid molecules in their external surface. Human patients given intravenous injections of such radiolabelled micellular particles showed tumors imaged by such method, without developing symptoms related to the micellular particles.

14 Claims, No Drawings

METHOD OF TARGETING TUMORS IN HUMANS

This application is a continuation of co-pending application Ser. No. 674,201, filed Nov. 23, 1984, now abandoned, and a continuation-in-part of application Ser. No. 663,503 and 663,550, filed Oct. 22, 1984, now abandoned, and Ser. No. 363,593, filed Mar. 30, 1982, now abandoned.

BACKGROUND OF THE INVENTION

1. Field of the Invention

This invention relates to a method of targeting and imaging tumors in humans, by the use of micellar particles such as phospholipid vesicles. More particularly, the invention relates to a method of introducing neutral or charged phospholipid micellar particles containing a radiolabeled marker into a patient to diagnose such tumors.

2. Description of Prior Art

Before various abnormalities in a patient's body can be diagnosed and treated, it is often necessary to locate the abnormalities. This is particularly true of abnormalities such as malignant tumors since the treatment is often on a localized basis. Thus, the location of the malignant tumor must be identified so that therapy can be directed to such cancer cells for treatment.

Various attempts have been made over an extended number of years to identify specific locations, such as tumors, by simple techniques. For example, it would be desirable to identify the location of cancer cells by a simple method involving the localization of a particular chemical at the specific site. It would also be desirable to treat the cancer by introducing modified chemicals into the patient's body and having such chemicals move to specific locations to combat the cancer cells at such locations. In spite of such attempts, however, simple delivery systems for targeting tumors in humans do not exist as yet.

Placing a chemotherapeutic drug in the body orally, subcutaneously or intravenously can result in harm to the normal cells in the body which take up the drug and a worsening in the patient's condition, without achieving the desired reduction in tumor cell activity. In the past, this toxicity to normal cells in the patient's body has been a major disadvantage in the treatment of tumors with chemotherapeutic agents. The lack of efficacy of such chemotherapy is also attributable to the failure of the freely circulating drug to localize within tumor cells before it is excreted or taken up by other cells in the body.

Prior attempts to improve treatment of tumors by chemotherapeutic agents have included encapsulation of such agents within biodegradable phospholipid micellar particles in the form of vesicles or liposomes. Encapsulation is thought to reduce potential toxicity from the circulating drugs. Researchers have also sought to utilize such encapsulation to selectively target tumors within a body for delivery of chemotherapeutics. However, until the invention disclosed in application Ser. No. 663,503, filed Oct. 22, 1984, "Method of Targeting a Specific Location in a Body," now abandoned, and its parent application Ser. No. 363,593, filed Mar. 30, 1982, now abandoned, efforts to locate or treat tumor cells with drug-encapsulating targeting particles have not been successful.

The inability to provide a satisfactory particle targeting method is believed to be due to the nature of the solid tumors and their metastases which are located in extravascular tissues. Thus, to accomplish targeting of intravenously injected radiolabelled or chemotherapeutic particles to the tumor cells, the particles must leave the normal circulation by crossing the blood vessel membranes to enter the extravascular tissues. This movement is known as "extravasation". In addition the encapsulated agent must cross the tumor cell membrane. Normally, small substances such as small molecular weight proteins and membrane-soluble molecules can cross cell membranes by a process known as passive diffusion. However, passive diffusion will not allow sufficient accumulation of larger particles carrying drugs within cells to reach therapeutic levels. Additionally, cells can actively transport materials across the membrane by a process such as pinocytosis wherein extracellular particles are engulfed by the membrane and released inside the cell. Entry of encapsulating particles into individual cells may occur by pinocytosis.

Progress in targeting tumors with chemotherapeutic drugs has been hampered by the inability to accomplish and detect movement of drug carriers across blood vessel membranes. In the usual case, large structures such as drug encapsulating vesicles cannot escape from blood vessels such as capillaries, and thus remain in circulation.

An understanding of extravasation, however, requires an examination of the structure of the vascular morphology of a tumor. Various blood vessels are associated with tumors, in particular capillaries. It is now known that tumor capillaries may exhibit alterations in their structure, such as fenestrations, as a result of tumor cell growth patterns. H.I. Peterson, *Vascular* and Extravascular Spaces in Tumors: *Tumor Vascular Permeability*, Chapter III, Tumor Blood Circulation, H.I. Peterson, Ed. (1979). Studies of tumor capillary permeability reveal morphologic variations in the capillaries which allow some substances to cross the capillary membrane Such variations include defects in vascular endothelium from poor cell differentiation, or breaks in vascular walls as a result of invading tumor cells. H.I. Peterson, *supra*. Notwithstanding such knowledge of tumor vascular morphology, researchers such as Peterson have concluded that transport of large molecules or materials across the tumor capillary wall occurs as a result of passive diffusion and that "concentrations of active drugs sufficient for therapeutic effect are difficult to reach". H.I. Peterson, supra, at 83.

Prior to such morphologic studies, early reports suggested that vesicles might undergo transcapillary passage across the capillary membranes into tumor cells. G. Gregoriadis, *Liposomes in Biological Systems*, Gregoriadis, Ed., Ch 2, (1980). However, available data indicated that the vesicles were unstable *in vivo* and that the radiolabel may have leaked, thus apparently prompting the two alternative theories of (1) longer circulation of vesicles in the blood with release of drugs at a slower rate or (2) interaction of the liposomes with the capillary walls without crossing the wall surface, which would result in the appearance of drugs at the tumor sites, but without drugs within tumor cells. *Id.* Other researchers simply concluded that the vesicles do not penetrate vascular walls after intravenous administration. B. Ryman et al., *Biol. Cell*, Vol. 47, pp. 71–80 (1983); G. Poste, *Biol. Cell*, Vol. 47, pp. 19–38 (1983).

Thus, although the prior art has recognized that vesicles carrying radiolabel markers or therapeutic drugs must cross vascular barriers to reach tumor cells, the experience of the art has taught that intravenous administration is not effective to deliver the vesicles to extravascular tumor cells. In the aforesaid application, Ser. No. 663,503, and parent application, Ser. No. 363,593, "Method of Targeting a Specific Location in a Body", the disclosures of which are incorporated herein by reference, a method is provided for targeting tumors *in vitro* and in animals, specifically, mice. In the present invention, a method is provided for enhancing extravasation of radiolabelled particles to tumor cells within humans, for the identification of such tumor sites.

SUMMARY OF THE INVENTION

In the method of this invention, phospholipid micellar particles such as vesicles that are pure (more than approximately 98% pure), i.e., stable to leakage *in vitro* and *in vivo* neutral phospholipid molecules are incorporated into small (less than 2000A°) micelles as a component of the external surface. The phospholipid molecules are radiolabelled to enhance the identity and the diagnosis of the tumor at the specific site.

In-111 labelled vesicles were injected intravenously into 13 patients with diagnoses of terminal cancer. Following intravenous injections of up to 275 mg of lipid and 500 microcuries of In-111, vesicles were rapidly taken up by the liver and spleen and a median of 12.5% of the injected vesicles remained within circulation at 24 hours. In no patient did symptoms develop related to vesicles following administration. Twelve of the thirteen patients had tumors imaged by this scan.

DETAILED DESCRIPTION OF THE INVENTION

As used herein, "micellar particle" and "micelles" refer to particles which result from aggregations of amphihilic molecules. In this invention preferred amphiphiles are biological lipids. Micelles are water-soluble aggregates of molecules with hydrophobic and hydrophilic portions (so-called amphiphilic molecules) which associate spontaneously. Such micelles can be in the form of small spheres, ellipsoids or long cylinders, and can also consist of bilayers with two parallel layers of amphiphilic molecules. Such bilayered micelles usually take the shape of spherical vesicles with an internal aqueous compartment. Useful compositions of these micelles include phospholipid molecules in the structure.

"Vesicle" refers to a micelle which is in a generally spherical form, often obtained from a lipid which forms a bilayered membrane and is referred to as a "liposome". Methods for forming these vesicles are, by now, well known in the art. Typically, they are prepared from a phospholipid, for example, distearoyl phosphatidylcholine, and may include other materials such as neutral lipids, for example, cholesterol, and also surface modifiers such as positively or negatively charged compounds.

The phospholipid molecules may constitute distearoyl phosphatidylcholine. The stability of the distearoyl phosphatidylcholine micelles may be enhanced by the incorporation of cholesterol. Positively charged molecules such as stearylamine or aminomannose or aminomannitol derivatives of cholesterol or negatively charged molecules such as dicetyl phosphate may also be incorporated into the vesicles.

When phospholipid micelles are introduced into the blood stream, the micelles move to the specific locations of cancerous growth in the patient's body. To enhance movement of the phospholipid vesicles to the specific locations, positively charged phospholipid vesicles may first be introduced into the patient's blood stream to block the macrophages or other phagocytic cells in the patient's body. The positively charged molecules bound to such phospholipid vesicles may be an aminomannose or aminomannitol derivative of cholesterol. Concurrently or after a suitable period of time such as approximately one (1) hour, other phospholipid vesicles may be introduced into the patient's blood stream to move to the specific locations in the body. Such phospholipid vesicles may include cholesterol and may be neutral or may be positively charged as by the inclusion of a stearylamine or aminomannose or aminomannitol derivative of cholesterol or may be negatively charged as by the inclusion of a dicetyl phosphate.

When the phospholipid vesicles are introduced into the body to target and image tumors, indium-111 may be used as the labelling agent. The indium-111 may be chelated to a suitable material such as nitrilotriacetic acid (NTA). NTA is advantageous because it forms a relatively weak bond with the indium-111. As a result, when the phospholipid vesicles reach the tumor and are lysed, the nitrilotriacetic acid is displaced by proteins at the tumor. Since the proteins form a stronger bond with indium-111, the indium-111 remains at the tumor for a long period of time (in excess of 24 hours), which provides for easy identification of the tumor over the extended period of time.

Materials and Methods

Liposome Preparation. Small unilamellar vesicles (SUV) with the ionophore A23187 were prepared from distearoyl phosphatidycholine (DSPC), cholesterol (Ch), dicetyl phosphate (DP), stearylamine (SA) and the 6-aminomannose (AM), and 6-aminomannitol (AML) derivatives of cholesterol, according to previous methods. Briefly, chloroform solutions of 10 mg lipid with the following molar ratios: DSPC:Ch, 2:1; DSPC:Ch:X, 4:1:1 where X=SA, DC or AML; and DSPC:Ch:AM, 8:3:1, were evaporated to dryness under nitrogen ($N_2$), and further dried under vacuum overnight. Each tube was filled with 0.6 ml 5mM phosphate buffered 0.9% saline, pH 7.4(PBS), containing 1mM nitrilotriacetic acid (NTA) and sonicated under $N_2$, for 5 to 15 minutes with a sonicator equipped with a titanium microtip.

Liposomes were annealed at 60° C for 10 minutes and centrifuged at 300×g for five to ten minutes. Liposomes were separated from unencapsulated NTA with a 30 x 1.5 cm Sephadex G-50 column. Liposome size was determined by laser light scattering. All vesicle types were shown by laser light scattering microscopy to have a mean diameter less than 0.1 microns (1000A°). For example, DSPC:Ch vesicles had a mean diameter of 528A°. However, vesicles as large as approximately 2000 Angstroms are believed to be satisfactory in obtaining the desired results of this invention, although the preferred range is approximately 500 to about 700A°.

The vesicles obtained as described above are chemically pure. By "chemically pure" it is meant that the materials which constitute phospholipid vesicles are more than 98% pure. For example, when the phospholipid chemical added is distearoyl phosphatidylcholine, this material is used at more than 98% purity. The same constraint holds for other components, such as cholesterol, which compose the vesicle. The phospholipid vesicles obtained as described above are stable to leakage in vitro and when injected into experimental animals.

The aminomannose and aminomannitol portions of these derivatives of cholesterol extend externally from the phospholipid particles. Thus, when such derivatives are incorporated or associated into the surfaces of vesicles or other micelles, an amine moiety is provided that extends approximately 5-15 Angstroms, preferably about 10 Angstroms, beyond the surface of the micelles. In the case of vesicles, it appears that the appropriate molecular design comprises a hydrophobic portion which serves to anchor the molecule within the vesicular bilayer, and a linking portion which is at least mildly hydrophilic which spans the requisite distance between the hydrophobic region and the amino functional group. The hydrophilicity is apparently required to prevent the link from internalizing within the bilayer also and thus serves to "extend" the amine from the surface. An example of a successful extended amine within the context of this invention is a 6-aminomannose cholesterol derivative such as, for example, 6-(5-cholesten-3,$\beta$-yloxy)hexyl6-amino-6-deoxyl-1-thio$\alpha$-D-mannopyranoside. In this example, the cholesterol portion provides the hydrophobic moiety, while the aminomannose is relatively hydrophilic. Other embodiments are also possible: other amino sugars attached to other cholesterol derivatives, for example, are equally suitable as alternative embodiments of the hydrophilic and hydrophobic portions. Polyamines and polyamino acids which can be bound covalently or associated by other means to the vesicle or other micelle surface may also be used.

The amino derivatives and cholesterol tend to impart stability to the phospholipid vesicles. Cholesterol may be included in the range of approximately 0% to 50% of cholesterol by weight and the remainder constituting the phospholipids. The charged molecules such as the stearylamine, the dicetyl phosphate and the aminomannose and aminomannitol derivatives of cholesterol may be included in the range of 0% to 20% by weight of the charged molecules and the remainder constituting the phospholipids.

The chemically pure liposome compositions discussed above are quite stable to leakage *in vitro* and *in vivo*. However, phospholipid mixtures such as egg lecithin form more fluid membranes than pure phospholipids. As a result, liposomes from natural lecithin mixtures are less stable to leakage of their contents than pure phopholipids.

In-111 Loading Procedure. Loading of In-111 into preformed liposomes was facilitated by the presence of A23187 in the lipid bilayer. In-111 was loaded into liposomes at 60–80° C in accordance with the procedure described by Mauh and Gamble, Anal. Biochem. 94, 302–307 (1979). Incubations were terminated by the addition of 10mM ethylenediaminetetraacetic acid (EDTA) in 10 mM phosphate buffered 0.9% sodium chloride, pH 7.4 (PBS), and free In-111 was separated from the loaded l:posomes by chromatography on Sephadex G-50. Up to 90% of the added In-111 could be incorporated into preformed liposomes by this technique, and specific activities of up to 300 uCi/mg lipid have been obtained.

All patients diagnosed by the process of this invention had biopsy-proven malignant disease diagnosed as incurable and a life-expectancy of less than two years. Patients received a dose of 500 $\mu$Ci of In-111 in varying amounts of vesicles (45–275 mg) such that the relationship between kinetics of distribution and clearance to lipid dose could be determined. The vesicles were of the following formulation:

| Per 100 mg lipid | mg |
|---|---|
| L-$\alpha$-distearoyl/phosphatidylcholine (DSPC) | 80.70 |
| Cholesterol | 19.30 |
| Nitrilotriacetic Acid (trisodium salt) | 0.03 |
| In-111Cl$_3$ ($\mu$Ci) | (250–1000 See Table 1) |
| Ionophore A23187 | 0.10 |

Patients were tested at the dosage levels indicated n Table 1. Three patients were admitted to each dose level until dose level three was attained. If toxicity was observed in any of the dose levels prior to level three, eight additional patients were to be entered at that dose level to determine adverse reaction frequency.

Twenty-four and forty-eight hours following the intravenous administration of vesicles over a three minute period, whole body and regional imaging was performed utilizing gamma camera-dedicated computer systems. Window settings were adjusted to include both 172 KeV and 247 KeV energy peaks for In-111 emissions.

TABLE 1

| LEVEL | DOSAGE LEVEL LIPID DOSE | 111 In DOSE |
|---|---|---|
| 1 | 50 mg | 500 $\mu$Ci |
| 2 | 100 mg | 500 $\mu$Ci |
| 3 | 200 mg | 500 $\mu$Ci |
| 4 | 200 mg | 750 $\mu$Ci* |
| 5 | 200 mg | 1000 $\mu$Ci* |

*dosage level not used to date

Tests were performed according to the schedule in Table 2.

TABLE 2

| | PARAMETERS FOLLOWED | | | | | |
|---|---|---|---|---|---|---|
| | Preinjection | 1 Hours | 4 Hours | 8 Hours | 24 Hours | 48 Hours | 72 Hours |
| Examination | × | | × | | × | × | |
| Scan | | | × (optional) | | × | × | × (optional) |
| CBC, Differential | × | | | | | × | |
| Platelet Count | × | | | | | × | |
| Chemistry-Profile and electrolytes (SMA 18) | × | | | | | × | |
| Chest X-Ray | × | | | | | × | |
| Serum Complement | × | | | | | × | |
| Urinalysis | × | | | | | × | |
| Blood Sample for Radioactivity | × | × | × | | × | × | × |

TABLE 2-continued

| | PARAMETERS FOLLOWED | | | | | |
|---|---|---|---|---|---|---|
| | Pre-injection | 1 Hours | 4 Hours | 8 Hours | 24 Hours | 48 Hours | 72 Hours |
| Urine Sample for Radioactivity | X | | X | X | | | X |
| Stool Sample for Radioactivity | | | | | | X | |

RESULTS

A. DESCRIPTION OF PATIENTS/DIAGNOSES

Thirteen patients (nine men and four women) were treated and the results were analyzed at the time of this report. Their ages ranged between 39-80. Patients were diagnosed as having primary cancers of the following sites:

| Site | No. of Patients |
|---|---|
| Lung | 3 |
| Breast | 3 |
| Prostate | 3 |
| Colon | 1 |
| Pancreas | 1 |
| Kidney | 1 |
| Lymphoma | 1 |

All patients except two (prostate cancer and oat cell lung cancer) had prior treatment for their cancer: ablative surgery, radiation therapy, chemotherapy and hormonal therapy were variously used to treat specific patients. Certain patients presented signs and symptoms that were known or suspected to be secondary to their cancers (e.g. bone pain and anemia).

B. DOSAGE DATA

Patients received intravenous injections of vesicles containing 45-275 mg of lipid and in all cases, 500 microcuries of indium-111. For kinetic studies, blood, urine and stool samples were collected over the first three days. Whole body and regional gamma camera images are obtained at 1-48 hours.

C. SAFETY DATA

None of the 13 patients developed symptoms within 72 hours after administration of the vesicles which were judged to be attributable to the test article. Patient #2 complained of weakness at 48 hours, having been recently placed in a new analgesic, Vistaril. Patient #3 complained of dizziness lasting 30 minutes which developed 8 hours post-injection. A neurological exam performed at 24 hours was within normal limits. The same patient's eosinophil count rose from 1% at baseline to 7% at 48 hours. Patient #6 developed a two degree increase in temperature and an increase in pulse (T 97.4, P 64 at baseline; T 99.9, P 90 at 8 hours). The temperature rise began at four hours and continued through 72 hours. The surgical insertion of Hickman catheter was judged to be the likely etiology. At 48 hours the same patient creatinine showed a slight increase from 0.7 mg/dl. to 0.9 mg/dl. Patient #9 showed an increase in glucose from baseline of 135 mg/dl to 194 mg/dl at 24 hours. Patient #13 showed an increase in eosinophils from 0% at baseline to 5% at 48 hours.

Otherwise, vital signs and physical examination, as well as blood and urine tests showed no change over the 72 hours following administration of the vesicles. Chest X-rays revealed no evidence of altered aeration or vascularity within the lungs.

D. RADIOPHARMACOKINETIC RESULTS

Radiokinetic determinations indicate that the liposomes were rapidly taken up by the liver and spleen. Within the first one to four hours, there was a large amount of radioactivity remaining within the blood stream as well, but by 24 hours after injection, a significant amount of vesicles had left the blood stream. A median of 12.5% of the injected vesicles remained within the circulation at 24 hours. Urinary excretion was quite small (median 0.95%) and fecal excretion was insignificantly small.

The radiation exposure to the whole body was 0.29 rads median. The patient with the highest amount of radiation exposure had only 0.30 rads whole body radiation. The dose limiting radiation exposures were liver and spleen. Usually liver exposure was slightly higher (7 patients) although in 5 patients, spleen exposure was slightly higher. The median exposure to the liver was 2.3 rads with the greatest exposure being 4.7 rads and the median exposure to the spleen was 1.6 rads with the highest exposure being 4.8 rads.

At 1-4 hours after administration, images demonstrated a vascular pool. At 24 and 48 hours, the liver and spleen had accumulated significant amounts of radioactivity, and the vasculate pool was minimal (exception patient #4 where the vascular pool remained high even at 48 hours.)

E. RESULTS AND IMAGING EFFICACY

Twelve of the thirteen patients had tumors imaged by this scan, including three patients with breast cancer, three patients with oat cell carcinoma of the lung, three patients with prostatic carcinoma, one patient with carcinoma of the rectum, one patient with carcinoma of the kidney, and one patient with malignant Lymphoma. Only in the patient with carcinoma of the pancreas was there no tumor image seen, and in that patient, the size of the tumors on the peritoneal surface was less than 5 mm.

Accumulating all of the organs which had tumor demonstated by standard techniques, 22 such organ sites were involved the tumor. Of those, 20 had tumors imaged by scans (false positive rate=9%). The patient with carcinoma of the pancreas did not have peritoneal soft tissue tumors identified, and a second patient with oat cell carcinoma of the lung metastatic to brain which had previously been heavily irradiated had no evidence of brain metastasis on liposome scan.

In the 82 instances of organ systems that were not clinically involved with tumor by standard techniques, there was 1 instance of imaging (of bone) by liposome scan (false positive rate=1.2%). The accuracy rate for vescan was 101/104 or 97%.

Organs which were imaged successfully by the vesicle scan included bone, lymph node, soft tissue including mediastinum, lung, liver, and spinal cord. A single patient with a brain tumor previously treated with radiation therapy was not able to be imaged.

Four cases of unsuspected tumors were observed. In patients with oat cell carcinoma, one patient with an unsuspected meningeal metastasis was identified, and another patient with an unsuspected liver metastasis was identified. One patient with carcinoma of the breast showed involvement diffusely over the right chest, and subsequently developed a malignant pleural effusion which was not present at the time of the vesicle scan. One patient with carcinoma of the prostate had a heterogeneous uptake of liposomes in the liver, and subsequently developed malignant hepatomegaly.

The results described above are summarized in Table 3 which follows:

TABLE 3

| Pt# | Disease | Prior* Treatment | Dose Lipid | Dose In-111 | % Blood in 4 h | % Blood in 24 h | % Exc. Urine | Radiation Exposures Liver | Radiation Exposures Spleen | Radiation Exposures Whole Body |
|---|---|---|---|---|---|---|---|---|---|---|
| 01 | Prostate | R,C,H | 62.6 | 0.5 | 65.7 | 28.5 | 1.4 | 2.0 | 0.6 | 0.27 |
| 02 | Pancreas | R,C | 44.5 | 0.5 | 15.0 | 1.3 | 0.7 | 4.7 | 3.1 | 0.30 |
| 03 | Breast | C,H | 56.8 | 0.5 | 40.4 | 12.5 | 1.2 | 2.5 | 2.2 | 0.28 |
| 04 | Breast | C | 82.1 | 0.5 | 86 | 64 | 0.9 | 0.8 | 1.2 | 0.28 |
| 05 | Lung, Oat Cell | R,C | 80 | 0.5 | 67.6 | 31.7 | 3.0 | 1.5 | 1.6 | 0.30 |
| 06 | Breast | R,H | 98.9 | 0.5 | 42 | 12.2 | 1.0 | 2.8 | 3.1 | 0.29 |
| 07 | Colon | R,C | 135 | 0.5 | 11.8 | 6.4 | 0.6 | 3.4 | 4.8 | 0.30 |
| 08 | Prostate | H | 102 | 0.5 | 50.6 | 27.1 | 0.6 | 1.4 | 1.4 | 0.30 |
| 09 | Kidney | C,H | 273 | 0.5 | — | 22.4 | 1.0 | 2.2 | 1.5 | 0.29 |
| 10 | Lung, Oat Cell | R,C | 200 | 0.5 | 51 | 5.5 | — | 2.1 | 1.5 | 0.20 |
| 11 | Prostrate | O | 173 | 0.53 | ND | 9.6 | 0.2 | 2.3 | 1.1 | 0.29 |
| 12 | Lung, Oat Cell | O | 276 | 0.5 | 5.9 | 2.0 | 2.0 | 3.8 | 1.8 | 0.29 |
| 13 | Lymphoma | O | 200 | 0.5 | ND | 14.4 | 0.7 | 2.4 | 4.4 | 0.30 |

| Pt# | Detection of tunor in organ** Bone Marrow | Bone | Node | Soft pleura, Tissue | Soft pleura, Lung | Liver | Brain | Spinal Cord | Comments | Autopsy Conf. | Toxicat. |
|---|---|---|---|---|---|---|---|---|---|---|---|
| 01 | 0.31 | TP | TN | TN | TN | TP | TN | | | 0 | 0 |
| 02 | 0.22 | TN | TN | FN | TN | TN | TN | | CT scan false in Pancreas | + | 0 |
| 03 | 0.28 | TN | TN | TP | TP | TN | TN | | Pleural effusion 1 month later | — | 0 |
| 04 | 0.34 | TP | TN | TP | TN | TN | TN | | | — | 0 |
| 05 | 0.38 | TN | TP | TN | TN | TP | FN | | | + | 0 |
| 06 | 0.28 | TP | TN | TN | TN | TN | TN | | | — | 0 |
| 07 | 0.16 | TN | TN | TP | TN | TN | TN | | | + | 0 |
| 08 | 0.32 | TP | TN | TN | TN | TN | TN | | | — | 0 |
| 09 | 0.36 | TN | TN | TP | TP | TN | TN | | | — | 0 |
| 10 | 0.19 | TN | TN | TN | TP | TN | TN | TP | | + | 0 |
| 11 | 0.29 | TP | TN | TP | TN | TN | TN | | | — | 0 |
| 12 | 0.25 | TP | TN | TN | TP | TN | TN | | | — | 0 |
| 13 | 0.28 | FP | TP | TN | TN | TN | TN | | | — | 0 |

As indicated above, the patients were given intravenous injections of up to approximately 275 milligrams of lipid and 500 microcuries of Indium-111. Other dose levels, however, are within the scope of the invention. Thus, the lipid dose may vary from approximately 40 milligrams to about 1 gram, with a range of about 100 to about 700 milligrams being preferred, and from about 200 to approximately 500 milligrams being especially preferred. The particular dose level of lipid will be determined on a case by case basis, with the amount being sufficient to present enough vesicles for tumor targeting and imaging and at the same time kept to as small an amount as reasonably possible since the vesicles constitute a foreign object in the human body.

In the examples herein reported, the dose of radiolabelled substance was 500 microcuries of Indium-111. It is to be understood, however, that other dose levels and other radiolabelled substances may be utilized. Thus, for example, radiolabelled materials such as gallium 67 (Ga-67), technetium 99m (Tc99m), and iodine 131 (I-131), may be utilized for imaging. It should also be understood that the particular dose level of radiolabelled substance will vary depending upon the specific substance utilized, as well as upon the preliminary diagnoses of the condition of the patient. Accordingly, with Indium-111, the dose level will typically range between approximately 0.5 to about 2.0 millicuries, whereas with gallium 67 and iodine 131, the dose will ordinarily be between about 2 and approximately 5 millicuries. With technetium 99m, however, which is known to be excreted much more readily and extensively than other radioactive elements, the dose will vary from approximately 5 to about 20 millicuries.

It will also be clear that the method of this invention, in addition to targeting and imaging tumors as described, is applicable in determining whether particles designed for therapy would move to a specific tumor site for a given patient. Moreover, it has been found that the method of this invention is particularly advantageous in that it does not image arthritis or inflammations as do other imaging techniques, and that only active tumor cells are imaged rather than cells that have been treated as by radiation or chemotherapy.

Although this invention has been described with reference to particular applications, the principles involved are susceptible to other applications which will be apparent to those skilled in the art. The invention is accordingly to be limited only by the scope of the appended claims.

We claim:
1. A method of targeting tumors in the breast, lung, prostate, kidney, colon, lymph, bone, lymph node, soft tissue including mediastinum, liver and spinal cord in humans comprising providing small umilamellar vesicles of less than about 2000Å comprising chemically pure phospholipid molecules that are stable to leakage in vitro and in vivo, incorporating a radioactive or chemotherapeutic agent into said vesicles and introducing such vesicles into the bloodstream of a human to obtain movement of the vesicles to the tumor for treating and/or imaging said tumor.

2. A method of targeting and imaging tumors in the breast, lung, prostate, kidney, colon or lymph of humans, comprising providing small unilamellar vesicles of less than about 2,000 Å comprising chemically pure phospholipid molecules that are stable to leakage in vitro and in vivo, incorporating a radioactive agent into said vesicles, introducing such vesicles into the bloodstream of a human to obtain movement of the vesicles to the tumor, and imaging said tumor.

3. A method according to claim 2 wherein the agent emits gamma radiation.

4. A method according to claim 3 wherein the agent comprises Indium-111.

5. A method according to claim 2 wherein the radioactive agent is Gallium 67, Technetium 99m or Iodine 131.

6. A method according to claim 2 wherein said phospholipid molecules comprise distearoyl phosphatidylcholine.

7. The method set forth in claim 6 wherein said vesicles further comprise cholesterol to enhance the stability of said vesicles.

8. The method of claim 2 wherein charged molecules are attached to said vesicles.

9. The method of claim 8 wherein said chemically pure phospholipid molecules are neutral and wherein the charged molecules are positively or negatively charged.

10. A method of targeting and imaging bone, lymph node, soft tissue including mediastinum, lung, liver and spinal cord in humans for the presence of tumors, comprising providing small unilamellar vesicles of less than about 2,000 Å comprising chemically pure phospholipid molecules that are stable to leakage *in vitro* and *in vivo*, incorporating a radioactive agent into said vesicles, introducing such vesicles into the bloodstream of a human to obtain movement of the vesicles to the tumor, and imaging said tumor.

11. A method of targeting and imaging metastatic tumors in humans, comprising providing small unilamellar vesicles of less than about 2,000 Å comprising chemically pure phospholipid molecules that are stable to leakage *in vitro* and *in vivo* incorporating a radioactive agent into said vesicles, introducing such vesicles into the bloodstream of a human to obtain movement of the vesicles to the tumor, and imaging said tumor.

12. A method of targeting and imaging metastatic tumors arising from a primary breast cancer, oat cell carcinoma, prostatic carcinoma, renal cell carcinoma, colon carcinoma or malignant lymphoma in humans, comprising providing small unilamellar vesicles of less than about 2,000 Å comprising chemically pure phospholipid molecules that are stable to leakage *in vitro* and *in vivo*, incorporating a radioactive agent into said vesicles, introducing such vesicles into the bloodstream of a human to obtain movement of the vesicles to the tumor, and imaging said tumor.

13. The method of claims 2, 10, 11 or 12 in which said micellar vesicles are less than approximately 1000 Å.

14. The method of claim 13 in which said vesicles are from about 500 to about 700Å.

* * * * *